US007972847B2

(12) United States Patent
Kalinski

(10) Patent No.: US 7,972,847 B2
(45) Date of Patent: Jul. 5, 2011

(54) MATURE TYPE-1 POLARIZED DENDRITIC CELLS WITH ENHANCED IL-12 PRODUCTION AND METHODS OF SERUM-FREE PRODUCTION AND USE

(76) Inventor: Pawel Kalinski, Wexford, PA (US)

( * ) Notice: Subject to any disclaimer, the term of this patent is extended or adjusted under 35 U.S.C. 154(b) by 0 days.

(21) Appl. No.: 12/138,324

(22) Filed: Jun. 12, 2008

(65) Prior Publication Data
US 2009/0004157 A1 Jan. 1, 2009

Related U.S. Application Data

(62) Division of application No. 10/842,185, filed on May 10, 2004, now abandoned.

(60) Provisional application No. 60/468,760, filed on May 8, 2003.

(51) Int. Cl.
*C12N 5/071* (2010.01)
*C12N 5/00* (2006.01)
*C12N 5/02* (2006.01)

(52) U.S. Cl. .................... 435/372; 435/373; 435/377

(58) Field of Classification Search .................. None
See application file for complete search history.

(56) References Cited

U.S. PATENT DOCUMENTS

| | | | |
|---|---|---|---|
| 4,832,959 A | 5/1989 | Engels et al. | |
| 5,437,994 A | 8/1995 | Emerson et al. | |
| 5,605,822 A | 2/1997 | Emerson et al. | |
| 5,624,895 A | 4/1997 | Sobel | |
| 5,635,386 A | 6/1997 | Palsson et al. | |
| 5,646,043 A | 7/1997 | Emerson et al. | |
| 5,670,147 A | 9/1997 | Emerson et al. | |
| 5,670,351 A | 9/1997 | Emerson et al. | |
| 5,763,215 A | 6/1998 | Blumberg | |
| 5,763,266 A | 6/1998 | Palsson et al. | |
| 5,780,021 A | 7/1998 | Sobel | |
| 6,204,022 B1 | 3/2001 | Johnson et al. | |
| 6,274,378 B1 * | 8/2001 | Steinman et al. | 435/377 |
| 6,326,198 B1 | 12/2001 | Emerson et al. | |

FOREIGN PATENT DOCUMENTS

WO WO02088328 11/2002

OTHER PUBLICATIONS

Sozzani et al., 1998, J. Immunol. vol. 161: 1083-1086.*
Luft et al., 2002, Int. Immunol. vol. 14: 367-380.*
Karaghiosoff et al., 2003, Central role for type I interferons and Tyk2 in lipopolysaccharide induced endotoxin shock. Nat. Immunol. vol. 4: 471-477.
Krug et al., 2001, Toll-like receptor expression reveals CpG DNA as a unique microbial stimulus for plasmacytoid dendritic cells which synergizes with CD40 ligand to induce high amounts of IL-12. Eur. J. Immunol. vol. 31: 3026-37.
Cella, M, Scheidegger D, Palmer-Lehmann K, Lane P, Lanzavecchia A, Alber G. 1996. Ligation of CD40 on dendritic cells triggers production of high levels of interleukin-12 and enhances T cell stimulatory capacity: T-T help via APC activation. J. Exp. Med. 184(2):747-52.
Langenkamp, A., Messi,M., Lanzavecchia,A. & Sallusto,F. (2000) Kinetics of dendritic cell activation: impact on priming of Th1, Th2 and nonpolarized T cells. Nat.lmmunol. 1: 311-316.
Schuler-Thurner, B, Schultz ES, Berger TG, Weinlich G, Ebner S, Woerl P, Bender A, Feuerstein B, Fritsch PO, Romani N, Schuler G. 2002. Rapid induction of tumor-specific type 1 T helper cells in metastatic melanoma patients by vaccination with mature, cryopreserved, peptide-loaded monocyte-derived dendritic cells. J. Exp. Med. 195(10):1279-88.
Shimizu, T, Berhanu A, Redlinger RE, Jr., Watkins S, Lotze MT, Barksdale EM, Jr. 2001. Interleukin-12 transduced dendritic cells induce regression of established murine neuroblastoma. J. Pediatr. Surg. 36 (8):1285-92.
Steinman, RM, Dhodapkar M. 2001. Active immunization against cancer with dendritic cells: the near future. Int. J. Cancer 94(4):459-73.
Thurner, B, Haendle I, Roder C, Dieckmann D, Kelkavoussi P, Jonulelit H, Bender A, Maczek C, Schreiner D, von Den DP, Brocker EB, Steinman RM, Enk A, Kampgen E, Schuler G. 1999. Vaccination with mage-3A1 peptide-pulsed mature, monocyte-derived dendritic cells expands specific cytotoxic T cells and induces regression of some metastases in advanced staae IV melanoma. J. Exp. Med. 190(11):1669-78.
Online Mendelian Inheritance in Man, OMIM (TM). Johns Hopkins University, Baltimore, MD. MIM No. {147570}: {Jul. 26, 2006}:.. World Wide Web URL: http://www.ncbi.nlm.nih.gov/omim/. NCBI Gene ID: 3458, The NCBI handbook [Internet]. Bethesda (MD): National Library of Medicine (US), National Center for Biotechnology Information; Mar. 2005 Chapter 19, Entrez Gene: A Directory of Genes. Available from http://www.ncbi.nlm.nih.gov/entrez/query. fcgi?db=Books.
NCBI Accession NP_000610, The NCBI handbook [Internet]. Bethesda (MD): National Library of Medicine (US), National Center for Biotechnology Information; Oct. 2002 Available from http:// www.ncbi.nlm.nih.gov/entrez/query.fcgi?db=Book.
NCBI Accession NM_000619, The NCBI handbook [Internet]. Bethesda (MD): National Library of Medicine (US), National Center for Biotechnology Information; Oct. 2002 Available from http:// www.ncbi.nlm.nih.gov/entrez/query.fcgl?db=Book.

(Continued)

*Primary Examiner* — Amy E Juedes
(74) *Attorney, Agent, or Firm* — Klarquist Sparkman, LLP

(57) ABSTRACT

The present invention discloses novel dendritic cell maturation-inducing cytokine cocktails, and methods for inducting type-1 polarized dendritic cells in serum-free conditions which enhance the desirable properties of DC1s generated in serum-supplemented cultures. The invention further discloses methods and systems using IFNγ and other ligands of the IFNγreceptor, in combination with IFNα (or other type I interferons), poly I:C, and other IFNα (and IFNβ) inducers to enhance the IL-12-producing properties of dendritic cells. More specifically, the present invention discloses type-1 polarized dendritic cells that have a unique combination of a fully-mature status and an elevated, instead of "exhausted", ability to produce IL-12p70 allows for the generation of fully-mature DC1s in serum-free AIM-V medium. The invention discloses systems that use the foregoing products and methods to facilitate the clinical application of DC1-based vaccines and the identification of novel factors involved in the induction of Th1 and CTL responses by DC1.

20 Claims, 12 Drawing Sheets

OTHER PUBLICATIONS

Online Mendelian Inheritance-in-Man, OMIM (TM). Johns Hopkins University, Baltimore, MD. MIM No. {147660}: {Mar. 3, 2006}:. World Wide Web URL:http://www.ncbi.nlm.nih.gov/omim/.

Rissoan, MC, Soumelis, V., Kadowaki, N., Grouard, G., Briere, F., Malefyt, R., Liu, YJ. 1999. Reciprocal Control of T Helper Cell and Dendritic Cell Differentiation. Science, vol. 283, No. 5405, pp. 1183-1186.

Colonna, M., Trinchieri, G., Liu, YJ. 2004. Plasmacytoid Dendritic Cells in Immunity. Nature Immunology. vol. 5. No. 12. pp. 1219-1226.

Asselin-Paturel, C., Trinchieri, G. 2005. Production of Type I Interferons: Plasmacytoid Dendritic Cells and Beyond. Jem, vol. 202, pp. 461-465.

McKenna, K., Beignon, AS, Bhardwaj, N. 2005. Plasmacytoid Dendritic Cells: Linking Innate and Adaptive Immunity. Journal of Virology. pp. 17-27.

Albert ML, Jegathesan M, Damell RB. Dendritic cell maturation is required for the cross-tolerization of CD8+T cells. Nature Immunology, vol. 2, No. 11, Nov. 2001, 1010-1017.

Alexopoulou L, Holt AC, Medzhitov R, Flavell RA. 2001. Recognition of double-stranded RNA and activation of NF-kappaB by Toll-like receptor 3. Nature 413(6857):732-8.

Banchereau J, Steinman RM. 1998. Dendritic cells and the control of immunity. Nature 392(6673):245-52.

Betz, M, Fox BS. 1991. Prostaglandin E2 inhibits production of Th1 lymphokines but not of Th2 lymphokines. J. Immunol. 146(1):108-13.

Bhardwaj, N. (1997) Interactions of viruses with dendritic cells: a double-edged sword. J. Exp. Med. 186, 795-799.

Cella, M, Scheidegger D, Palmer-Lehmann K, Lane P, Lanzavecchia A, Alber G. 1996. Ligation of CD40 on dendritic cells triggers production of high levels of interleukin-12 and enhances T cell stimulatory capacity: T-T help via APC activation. J. Exp. Med. 184(2):747-52.

Chikamatsu, K, Nakano K, Storkus WJ, Appella E, Lotze MT, Whiteside TL, DeLeo AB. 1999. Generation of anti-p53 cytotoxic T lymphocytes from human peripheral blood using autologous dendritic cells. Clin. Cancer Res. 5(6): 1281-8.

De Jong, EC, Vieira PL, Kalinski P, Schuitemaker JH, Tanaka Y, Wierenga EA, Yazdanbakhsh M, Kapsenberg ML. 2002, Microbial compounds selectively Induce Th1 cell-promoting or Th2 cell-promoting dendritic cells in vitro with diverse th cell-polarizing signals. J. Immunol. 168(4):1704-9.

Del Prete, GF, De Carli M, Ricci M, Romagnani S. 1991. Helper activity for immunoglobulin synthesis of T helper type 1 (Th1) and Th2 human T cell clones: the help of Th1 clones is limited by their cytolytic capacity. J. Exp. Med. 174 (4):809-13.

De Smedt, T., Van Mechelen,M., De Becker,G., Urbain,J., Leo,O. & Moser,M.. (1997) Effect of interleukin-10 on dendritic cell maturation and function. Eur. J. Immunol. 27, 1229-1235.

Dhodapkar, MV, Steinman RM, Krasovsky J, Munz C, Bhardwaj N. 2001. Antigen-specific inhibition of effector T cell function in humans after injection of immature dendritic cells. J. Exp. Med. 193(2):233-8.

Friberg, DD, Bryant JL, Whiteside TL. 1996. Measurements of Natural Killer (NK) Activity and NK-Cell Quantification. Methods 9(2):316-26.

Harris, SG, Padilla J, Koumas L, Ray D, Phipps RP. 2002. Prostaglandins as modulators of immunity. Trends Immunol. 23(3):144-50.

Hilkens, C.M., Kalinski,P., de Boer,M. & Kapsenberg.M.L. (1997) Human dendritic cells require exogenous interleukin-12-Inducing factors to direct the development of naive T-helper cells toward the Th1 phenotype. Blood 90, 1920-1926.

Jonuleit, H., Kuhn,U., Muller,G., Steinbrink,K., Paragnik,L., Schmitt,E., Knop,J. & Enk,A.H.. (1997) Pro-inflammatory cytokines and prostaglandins induce maturation of potent immunostimulatory dendritic cells under fetal calf serum-free conditions. Eur. J. Immunol. 27, 3135-3142.

Jonuleit, H, Giesecke-Tuettenberg A, Tuting T, Thumer-Schuler B, Stuge TB, Paragnik L, Kandemir A, Lee PP, Schuler G. Knop J, Enk Ah. 2001. A comparison of two types of dendritic cell as adjuvants for the induction of melanoma-specific T-cell responses in humans following intranodal injection. Int. J. Cancer 93(2):243-51.

Jonuleit, H, Schmitt E, Schuler G, Knop J, Enk AH. 2000. Induction of interleukin 10-producing, nonproliferating CD4(+) T cells with regulatory properties by repetitive stimulation with allogeneic immature human dendritic cells. J. Exp. Med. 192(9):1213-22.

Ju ST, Cui H, Panka DJ, Ettinger R, Marshak-Rothstein A. Participation of target Fas protein in apoptosis pathway induced by CD4+ Th1 and CD8+ cytotoxic T cells. Proc. Natl. Acad. Sci., vol. 91, 4185-4189, May 1994, Immunology.

Kalinski, P, Hilkens CM, Snijders A, Snijdewint FG, Kapsenberg ML. 1997. IL-12-deficient dendritic cells, generated in the presence of prostaglandin E2, promote type 2 cytokine production in maturing human naive T helper cells. J. Immunol. 159(1):28-35.

Kalinski, P, Schuitemaker JH, Hilkens CM, Kapsenberg ML. 1998. Prostaglandin E2 induces the final maturation of IL-12-deficient CD1a+CD83+ dendritic cells: the levels of IL-12 are determined during the final dendritic cell maturation and are resistant to further modulation. J. Immunol. 161(6):2804-9.

Kalinski, P., Schuitemaker,J.H., Hilkens,C.M., Wierenga,E.A. & Kapsenberg,M.L. (1999) Final maturation of dendritic cells is associated with impaired responsiveness to IFN-gamma and to bacterial IL-12 inducers: decreased ability of mature dendritic cells to produce IL-12 during the Interaction with Th cells. J. Immunol. 162, 3231-3236.

Kalinski, P, Smits,H.H., Schuitemaker,J.H., Vieira,P.L., van Eijk,M., de Jong,E.C., Wierenga,E.A. & Kapsenberg,M.L.. (2000) IL-4 is a mediator of IL-12p70 induction by human Th2 cells: reversal of polarized Th2 phenotype by dendritic cells. J. Immunol. 165, 1877-1881.

Kalinski, P, Vieira PL, Schuitemaker JH, de Jong EC, Kapsenberg ML. 2001. Prostaglandin E(2) is a selective inducer of interleukin-12 p40 (IL- 12p40) production and an inhibitor of bioactive IL-12p70 heterodimer. Blood 97(11):3466-9.

Langenkamp, A., Messi,M., Lanzavecchia,A. & Sallusto,F. (2000) Kinetics of dendritic cell activation: impact on priming of Th1, Th2 and nonpolarized T cells. Nat.lmmunol. 1: 311-316.

Mailliard, RB, Egawa S, Cai Q, Kalinska A, Bykovskaya SN, Lotze MT, Kapsenberg ML, Storkus WJ, Kalinski P. 2002. Complementary dendritic cell-activating function of CD8+ and CD4+ T cells: helper role of CD8+ T cells in the development of T helper type 1 responses. J. Exp. Med. 195(4):473-83.

McRae, B.L., Semnani,R.T., Hayes,M.P. & van Seventer,G.A. Type I IFNs inhibit human dendritic cell IL-12 production and Th1 cell development. J. Immunol. 160, 4298-4304 (1998).

Nestle, FO, Alijagic S, Gilliet M, Sun Y, Grabbe S, Dummer R, Burg G, Schadendorf D. 1998. Vaccination of melanoma patients with peptide- or tumor lysate-pulsed dendritic cells. Nat. Med. 4(3):328-32.

Parmiani, G, Castelli C, Dalerba P, Mortarini R, Rivoltini L, Marincola FM, Anichini A. 2002. Cancer immunotherapy with peptide-based vaccines: what have we achieved? Where are we going? J. Natl. Cancer Inst. 94(11):805-18.

Peters, J.H., Xu,H., Ruppert,J., Ostermeier,D., Friedrichs,D. & Gieseler,R.K.. (1993) Signals required for differentiating dendritic cells from human monocytes in vitro. Adv. Exp. Med. Biol. 329, 275-280.

Robinson, RA, DeVita VT, Levy HB, Baron S, Hubbard SP, Levine AS. 1976. A phase I-II trial of multiple-dose polyriboinsic-polyribocytidylic acid in patients with leukemia or solid tumors. J. Natl. Cancer Inst. 57(3):599-602.

Sallusto, F, Lanzavecchia A. 1994. Efficient presentation of soluble antigen by cultured human dendritic cells is maintained by granulo-cyte/macrophage colony-stimulating factor plus interleukin 4 and downregulated by tumor necrosis factor alpha. J. Exp. Med. 179(4):1109-18.

Schuler-Thurner, B. Dieckmann D, Keikavoussi P, Bender A, Maczek C, Jonuleit H, Roder C, Haendle I, Leisgang W. Dunbar R. Cerundolo V, von Den DP, Knop J. Brocker EB. Enk A. Kampgen E. Schuler G. 2000. Mage-3 and influenza-matrix peptide-specific cytotoxic T cells are inducible in terminal stage HLA-A2.1+ melanoma patients by mature monocyte-derived dendritic cells. J. Immunol. 165(6):3492-6.

Schuler-Thurner, B, Schultz ES, Berger TG, Weinlich G, Ebner S, Woerl P, Bender A, Feuerstein B, Fritsch PO, Romani N, Schuler G. 2002. Rapid induction of tumor-specific type 1 T helper cells in metastatic melanoma patients by vaccination with mature, cryopreserved, peptide-loaded monocyte-derived dendritic cells. J. Exp. Med. 195(10):1279-88.

Shimizu, T, Berhanu A, Redlinger RE, Jr., Watkins S, Lotze MT, Barksdale EM, Jr. 2001. Interleukin-12 transduced dendritic cells induce regression of established murine neuroblastoma. J. Pediatr. Surg. 36 (8):1285-92.

Shurin, MR, Esche C, Peron JM, Lotze MT. 1997. Antitumor activities of IL-12 and mechanisms of action. Chem. Immunol. 68:153-74.

Smits, HH, de Jong EC, Schuitemaker JH, Geijtenbeek TB, van Kooyk Y, Kapsenberg ML, Wierenga EA. 2002. Intercellular adhesion molecule-1/LFA-1 ligation favors human Th1 development. J. Immunol. 168 (4):1710-6.

Snijders, A, Kalinski P, Hilkens CM, Kapsenberg ML. 1998. High-level IL-12 production by human dendritic cells requires two signals. Int. Immunol. 10(11):1593-8.

Snijdewint, FG, Kalinski P, Wierenga EA, Bos JD, Kapsenberg ML. 1993. Prostaglandin E2 differentially modulates cytokine secretion profiles of human T helper lymphocytes. J. Immunol. 150(12):5321-9.

Steinman, RM, Dhodapkar M. 2001. Active immunization against cancer with dendritic cells: the near future. Int. J. Cancer 94(4):459-73.

Tahara, H, Zeh HJ, III, Storkus WJ, Pappo I, Watkins SC, Gubler U, Wolf SF, Robbins PD, Lotze MT. 1994. Fibroblasts genetically engineered to secrete interleukin 12 can suppress tumor growth and induce antitumor immunity to a murine melanoma in vivo. Cancer Res. 54(1):182-9.

Tatsumi, T, Kierstead LS, Ranieri E, Gesualdo L, Schena FP, Finke JH, Bukowski RM, Mueller-Berghaus J, Kirkwood JM, Kwok WW, Storkus WJ. 2002. Disease-associated bias in T helper type 1 (Th1)/Th2 CD4(+) T cell responses against MAGE-6 in HLA-DRB10401(+) patients with renal cell carcinoma or melanoma. J. Exp. Med. 196(5):619-28.

Thurner, B, Haendle I, Roder C, Dieckmann D, Keikavoussi P, Jonuleit H, Bender A, Maczek C. Schreiner D, von Den DP, Brocker EB, Steinman RM, Enk A, Kampgen E. Schuler G. 1999. Vaccination with mage-3A1 peptide-pulsed mature. monocyte-derived dendritic cells expands specific cytotoxic T cells and induces regression of some metastases in advanced stage IV melanoma. J. Exp. Med. 190(11):1669-78.

Trinchieri, G. 1998a. Interleukin-12: a cytokine at the interface of inflammation and immunity. Adv. Immunol. 70:83-243.

Trinchieri, G. 1998b. Proinflammatory and immunoregulatory functions of interleukin-12. Int. Rev. Immunol. 16(3-4):365-96.

Tuting, T, Wilson CC, Martin DM, Kasamon YL, Rowles J, Ma DI, Slingluff CL, Jr., Wagner SN, van der BP, Baar J, Lotze MT, Storkus WJ. Autologous human monocyte-derived dendritic cells genetically modified to express melanoma antigens elicit primary cytotoxic T cell responses in vitro: enhancement by cotransfection of genes encoding the Th1-biasing cytokines IL-12 and IFN-alpha. Journal of Immunology, 1998, 160: 1139-1147.

Van Der Pouw, Kraan TC, Boeije LC, Smeenk RJ, Wijdenes J, Aarden LA. 1995. Prostaglandin-E2 is a potent inhibitor of human interleukin 12 production. J. Exp. Med. 181(2):775-9.

Vieira, PL, de Jong EC, Wierenga EA, Kapsenberg ML, Kalinski P. 2000. Development of Th1-inducing capacity in myeloid dendritic cells requires environmental instruction. J. Immunol. 164(9):4507-12.

Wierenga, EA, Snoek M, Jansen HM, Bos JD, van Lier RA, Kapsenberg ML. Human atopen-specific types 1 and 2 T helper cell clones. Journal of Immunology, No. 9, Nov. 1, 1991, vol. 147, 2942-2949.

Zitvogel, L, Mayordomo JI, Tjandrawan T, DeLeo AB, Clarke MR, Lotze MT, Storkus WJ. 1996. Therapy of murine tumors with tumor peptide-pulsed dendritic cells: dependence on T cells, B7 costimulation, and T helper cell 1-associated cytokines. J. Exp. Med. 183(1):87-97.

David, M.,1995. Transcription Factors in Interferon Signaling. Pergamon., Pharmac. Ther. vol. 65 149-161.

Luft, T. et al. 2002. Funtionally Distinct Dendritic Cell (DC) Populations Induced by Physiologic Stimuli: Prostaglandin E2 Regulates the Migratory Capacity of Specific DC Subsets. Immunobiology. Blood, vol. 100, No. 4. 1362-1372.

Mailliard, R. et al. 2004. a-Type-1 Polarized Dendritic Cells: A Novel Immunization Tool With Optimized CTL-Inducing Activity. Cancer Research 64, 5934-5937.

Platanias, L. et al. 1999. Signaling Pathways Activated by Interferons. Elsevier. Experimental Hematology 27. 1583-1592.

Scandella, E. et al. 2002. Prostaglandin E2 is a Key Factor for CCR7 Surface Expression and Migration of Monocyte-Derived Dendritic Cells. Immunobiology. Blood, vol. 100, No. 4. 1354-1361.

Verdijk, Rob M., et al., *Polyriboinosinic Polyribocytidylic Acid (Poly(I:C)) Induces Stable Maturation of Functionally Active Human Dendritic Cells*[1]. Article: The Journal of Immunology, 1999, 163: 57-61. Copyright © 1999 by The American Association of Immunologists, 0022-1767/99. United States of America.

* cited by examiner

A. Maturation markers

B. CCR7 expression

A.

B.

MATURE TYPE-1 POLARIZED DENDRITIC CELLS WITH ENHANCED IL-12 PRODUCTION AND METHODS OF SERUM-FREE PRODUCTION AND USE

CROSS REFERENCE TO RELATED APPLICATIONS

This is a divisional of U.S. patent application Ser. No. 10/842,185, filed May 10, 2004, now abandoned which in turn claims the benefit of U.S. Provisional Patent Application No. 60/468,760, filed May 8, 2003, entitled "MATURE TYPE-1 POLARIZED DENDRITIC CELLS WITH ENHANCED IL-12 PRODUCTION AND METHODS OF SERUM-FREE PRODUCTION AND USE". U.S. patent application Ser. No. 10/842,185 is incorporated by reference herein in its entirety.

STATEMENT AS TO RIGHTS TO INVENTIONS MADE UNDER FEDERALLY SPONSORED RESEARCH AND DEVELOPMENT

Portions of the present invention were made with support of the United States Government via a grant from the National Cancer Institute under grant number 1R01CA82016. The U.S. Government may therefore have certain rights in the invention.

BACKGROUND

1. Field of the Invention

The invention relates to methods of generating mature dendritic cells with enhanced IL-12 production and compositions and systems for such dendritic cells.

2. Discussion of the Background

Dendritic cells (DCs), the most potent antigen presenting cells, are effective inducers of protective immunity against infectious diseases and cancer (Banchereau & Steinman 1998). The adjuvant function(s) of DCs has prompted intense interest in the use of DCs as a vaccine component, particularly after the advent of in vitro methods to generate large numbers of DCs from monocytes (Peters et al 1993, Sallusto & Lanzavecchia 1994). Over the past years, DC-based vaccines have been increasingly applied in the clinical treatment of cancer patients (Steinman et al., 2001; Parmiani et al., 2002). Following the initial success of the multi-epitope melanoma trial (Nestle et al 1998; 30% objective clinical responses), DCs have been used successfully to treat patients with melanoma, lymphoma and renal cell carcinoma (reviewed: Steinman et al., 2001; Parmiani et al., 2002). However, the overall clinical response rates do not exceed the predictable 15% observed for alternate immunotherapies (idem), which is below expectations, highlighting the need for improved design of DC-based vaccines, including the selection of the most appropriate types of DCs.

Although some of the early studies with DC-based vaccines successfully used FCS-based protocols (Nestle et al., 1998), the need to obtain the vaccine-applied DCs in possibly best-defined conditions (and to overcome potential reproducibility and regulatory issues) prompted the development of serum-free approaches to grow DCs.

Extensive research of recent years convincingly demonstrated that the effective induction of anti-tumor CTL responses requires the participation of fully-mature DCs because immature DCs are either ineffective, poorly immunogenic, or induce undesirable IL-10-producing regulatory T cells (Jonuleit et al 2000, Dhodapkar et al 2001). These considerations, in conjunction with the desire to use the most strictly-defined and reproducible conditions of DC generation for human use, established the dominant position of the "complete cytokine cocktail" composed of the combination of inflammatory cytokines IL-1β, TNFα, IL-6, and $PGE_2$ (Jonuleit et al. 1997), as the "gold standard" of DCs used in cancer immunotherapy.

Fully-mature DCs induced by the combination of inflammatory cytokines IL-1β, TNFα, IL-6, and $PGE_2$ (Jonuleit et al. 1997) have been consistently observed as superior to immature DCs in promoting a higher degree of specific T cell priming in vitro and in vivo (Jonuleit et al., 2001, Schuler-Thumer et al., 2000, Schuler-Thumer et al., 2002, Thurner et al., 1999, Dhodapkar et al., 2001).

Unfortunately, the maturation stage of DCs obtained in the currently-available protocols inversely correlates with their ability to produce IL-12p70 (Kalinski et al., 1999, Langenkamp et al., 2000), the cytokine with powerful anticancer Th1- and CTL-inducing properties (Trinchieri, 1998b); (Shurin et al., 1997).

Induction of Ag-specific CD8 T cells and Th1-type CD4 T cells depends on the ability of DCs to provide CD4 and CD8 T cell precursors with high levels of co-stimulation and with interleukin-12 (IL-12), the major DC-produced anti-tumor cytokine. Previous work with DC transduced with IL-12 genes demonstrated that high IL-12-producing DCs are effective inducers of tumor rejection in experimental animals. However, use of IL-12 transduced DC in humans creates substantial logistic problems. It also carries potential risks associated with the administration of genetically-manipulated material and the risks of direct IL-12 toxicity and of deregulating the immune system due to uncontrolled IL-12 production.

Many have attempted to generate DC's using a variety of methods. For example, U.S. Pat. Nos. 5,851,756, 5,994,126 and 5,475,483 (Steinman, Inaba and Schuler) disclose methods for generating DCs from proliferating precursors and their maturation. Further, U.S. Pat. No. 5,866,115 discloses a method of developing DCs from DC34+ blood progenitors and U.S. Pat. Nos. 6,228,640 and 6,251,665 disclose a means of loading DCs developed from CD34+ progenitors with RNA or its expression products as a mean of achieving the expression of tumor-related or other target-related antigens. Similarly, U.S. Pat. No. 6,121,044 teaches a means of developing DC in bulk monocytes-depleted PBMC cultures. These patents focus on particular methods of generating immature dendritic cells rather than the particular conditions of the maturation of dendritic cells. More importantly, none of these patents disclose or teach the generation of dendritic cells with the unique properties described in the present invention. Specifically, none of the patents disclose or teach the combination of type I and type II interferons (such as IFNα and IFNγ), as a part of the cytokine cocktail used to produce fully mature DCs with high IL-12 producing capacity.

Thus, despite the efforts of many, the desirable combination of high immunostimulatory activity with a high capacity to produce IL-12p70 could not be attained by all previous DC-based vaccines which have employed either mature DCs exhibiting high stimulatory/low IL-12-secreting functions or immature DCs that display low stimulatory/high IL-12 secretion functions.

It is known in the art that the presence of IFN-γ during the either LPS-induced or IL-1β/TNFα-induced DC maturation, results in the induction of stable type-1 polarized DCs (DC1s) that produce up to 100-fold higher levels of IL-12p70 in response to subsequent CD40L stimulation or the interaction with CD40L-expressing $CD4^+$ Th cells (Vieira et al., 2000, Mailliard et al., 2002). Unfortunately, the original DC1-inducing cytokine cocktail, composed of IL-1β, TNFα, and IFN-γ (Vieira et al 2000), does not allow for the induction of DC1s in serum-free media, which is desirable for clinical application.

DCs in the periphery can be exposed to a variety of environmental "triggers" that result in DC "maturation" and upregulation of factors critical to antigen-specific T-cell activation, including IL-12 production. In some cases, these signals are transmitted through Toll-like receptor ("TLRs") and other cell-surface receptors expressed by DCs.

It is an object of the present invention to provide a means of triggering DC maturation through innate signaling pathways to enable DCs to express potent DC1-type function, regardless of the presence of factors present in serum, enabling in vitro derivation of DC1s for clinical applications.

It is an object of one preferred embodiment of the present invention to add at least one from the group of IFNα or IFNβ (type I interferons) or a type I interferon inducing factor such as polyinosinic:polycytidylic acid (poly-I:C) to the "classical" DC1-inducing cocktail (INFα/IL-1β/IFNγ) and to provide a means for generating fully-mature DC1s in serum-free AIM-V medium.

It is further an object of the present invention to provide an alpha-type-1 DC to induce up to 50-fold higher levels of cancer-specific CTLs, and higher cytolytic activity of Th1 or NK cells compared to the current "gold standard" DCs (matured by IL-1β/TNFα/IL-6/PGE2; Jonuleit et al., 1997).

SUMMARY

The present invention discloses novel dendritic cell ("DC") maturation-inducing cytokine cocktails, and means for inducting type-1 polarized dendritic cells ("DC1s") in serum-free conditions which enhance the desirable properties of DC1s generated in serum-supplemented cultures. The invention further discloses the use of IFNγ and other ligands of the IFNγ receptor, in combination with IFNα (or other type I interferons, such as IFNβ, known to bind to the same receptor), poly I:C, and other IFNα (and IFNβ) inducers to enhance the IL-12-producing properties of DCs. The invention also discloses the use of DC1s to induce Ag-specific T cells against tumors, intracellular pathogens, and atopic allergens for active and passive immunotherapy, immunomonitoring and research purposes. More specifically, the present invention discloses type-1 polarized DCs (DC1s) that have a unique combination of a fully-mature status and an elevated, instead of "exhausted", ability to produce IL-12p70. These properties allow these DC1s to selectively induce high-intensity Th1-, CTL-, and NK cell-mediated type-1 immune responses, including those desirable in the treatment of cancer. Another preferred embodiment of the present invention shows that the inclusion of IFNα and/or poly-I:C to the "classical" DC1-inducing cocktail (TNFα/IL-1β/IFNγ) allows for the generation of fully-mature DC1s in serum-free AIM-V medium. In other preferred embodiments, the present invention discloses serum-free protocols of DC1 generation that facilitate the clinical application of DC1-based therapies and the identification of novel factors involved in the induction of Th1-, CTL-, and NK cell responses by DC1.

Sequence Listing

The Sequence Listing is submitted as an ASCII text file [8088-81340-01 _Sequence_Listing.txt, November 16, 2010, 912 bytes], which is incorporated by reference herein.

DETAILED DESCRIPTION

To boost the immunogenic capacity of DCs and their ability to induce high-intensity Th1 and CTL-mediated type-1 immune responses, the present invention combines within one DC type a fully-mature status and a high ability to produce high levels of IL-12p70. In contrast to current methodologies in which the final maturation of DCs induced by typical stimuli is associated with reduced ability to produce IL-12 (Kalinski et al., 1999, Langenkamp et al., 2000), the present invention provides for concomitant exposure of immature DC to a maturation-inducing stimulus and to IFNγ which results in a strong enhancement of the subsequent ability of mature DC to produce IL-12 and to induce Th1-dominated responses (Vieira et al., 2000, Mailliard et al., 2002), and more specifically the cancer-specific CTL responses.

Further, although current DC1-inducing protocols are ineffective in serum-free conditions, the present invention provides that IFN, a member of type I interferon family, and poly-I:C, an IFNα-inducing factor, can both synergize with the IFN-γ-based type-1-polarizing cocktails, allowing for the induction of fully-mature type-1 polarized DC in serum-free conditions. The present invention provides for adding at least one of the group of IFNα and poly-I:C to a cocktail of TNFα/IL-1β/IFNγ in either a serum-free culture or a serum-supplemented culture depending on the specifications of the application.

Although the current DC-based vaccines rely on either immature DCs (with high ability to produce IL-12 but low stimulatory capacity), or mature DCs (with high stimulatory function, but reduced IL-12 production), the current invention describes a method that provides a means of producing both of these desirable features within a single DC1-based vaccine preparation.

In addition, the DC1s of the present invention exhibit a stable phenotype that is resistant to tumor-associated immunosuppressive factors, including IL-10 and $PGE_2$ (Kalinsid et al., 1998, Vieira et al., 2000). Moreover, DC1s of the present invention can produce IL-12p70 upon the interaction with $CD4^+$ T cells that are unable to produce IFNγ or other IL-12 co-inducing factors (Vieira et al., 2000). These DC1s are able to boost the clinical efficacy of cancer vaccines, despite the presumed immunosuppressive environment of immunocompromised cancer patients and their undesirable bias towards Th2-type immunity (Tatsumi et al., 2002).

Previous work with DC transduced with IL-12 genes demonstrated that high IL-12-producing DC are effective inducers of tumor-specific Th1 cells and CTLs and of tumor rejection in experimental animals (Zitvogel et al., 1996, Shimizu et al., 2001, Tuting et al.,) (Chikamatsu et al., 1999, Tahara et al., 1994). However, use of IL-12 transduced DC in humans suffers from substantial logistic problems. It also carries potential risks associated with the administration of genetically-manipulated material as well as the risks of direct IL-12 toxicity and of deregulating the immune system, due to uncontrolled IL-12 production.

The present invention provides a feasible way to generate fully mature DC with high IL-12 producing capacity without any genetic manipulation which overcomes the above obstacles, paving the way to wide application of DC1-based immunotherapies. The present invention's DC1-inducing cytokine cocktails are based on the factors which are either FDA-approved drugs, or have been approved by FDA for use as investigational drugs. Poly I:C have been used as a biologic response modifier in cancer, as early as in 1976 in NCI, by the group of A. S. Levine (Robinson et al., 1976), and subsequently in many other clinical trials, which demonstrated its safety. Similar, IFNα, IFNγ, IL-1β, and TNFα, are commonly-used biological agents, approved as drugs or investigational drugs.

Because IL-12 production has been shown to be important for the control of numerous intracellular pathogens, including *Leishmania, Listeria, Mycobacterial* infections, and many viruses, the DC1s of the present invention can be used to treat chronic infections, including the infections with HIV, EBV, CMV, HCV, HBV, mycobacteria (e.g. tuberculosis and lepromatous leprosy), or parasites (e.g. Leishmaniasis). Further, the powerful Th1- and CTL-inducing DC1s of the present invention may be used to revert undesirable Th2 bias, and the B cell production of pathogenic antibodies in atopic allergies (e.g. manifested as atopic dermatitis or asthma) or autoimmune diseases, e.g. SLE, Graves disease, IgA nephropathy, or autoimmune trombocytopenia. In contrast to Th2 cells, Th1 cells and CTLs produced by the present invention have a limited or no ability to support antibody production, and can limit this process by killing the antibody-producing B cells (Wierenga et al, Ju et al, Del Prete et al 1991).

In addition to their therapeutic use as vaccine carriers, the DC1s of the present invention will be a useful tool in the development of additional novel therapies. The superior ability of DC Is of the present invention to activate Ag-specific T cells in vitro enables them to be used as immunomonitoring tools with superior sensitivity in detecting low-intensity (or suppressed) immune responses, facilitating the analysis of immune responses in patients with cancer, HIV, and other diseases.

The serum-free protocols of DC1 induction of the present invention can serve as a tool for defining the exact mechanism(s) of the DC1-mediated induction of Th1 cells and CTLs. Although IL-12's key role in the ability of DC to induce Th1 responses has been demonstrated, it is likely that other factors may also be important in this respect. The serum-free DC1 generation protocols of the current invention enable the use of the powerful proteomic approach to analyze the unique pattern of DC1 interaction with other immune cells. This may lead to the identification of novel Th1- and CTL-inducing factors, with potential additional therapeutic applications.

The current data indicate the feasibility of generating fully-mature DC in the absence of PGE2, the maturation-enhancing factor with particularly-pronounced IL-12 antagonistic activity (Kalinski et al., 1997, Kalinski et al., 1998, Kalinski et al., 2001). The lack of the absolute requirement for PGE2 in the induction of functional mature DC is in accord with the apparent lack of immunosuppressive activity of COX-1 and COX-2-inhibitors, used as non-steroid anti-inflammatory drugs. On the contrary, PGE2 has been shown to suppress the production of IL-12p70 in several types of APC including DCs (van Der Pouw Kraan T C et al., 1995); Kalinski et al., 1997), can directly suppresses Th1-cells (Betz & Fox, 1991, Snijdewint et al., 1993), and may play a role in tumor-associated immune dysfunction (reviewed in (Harris et al., 2002).

Although other IFNs signaling through type I IFN receptors are known to activate the similar signaling pathways and exert similar biologic effects, the present invention allows testing which of particular pathways induced by type I interferons (including STAT-1, STAT-2, STAT-3, STAT-4 and NFκB) remain critical for DC1 induction. Definition of the molecular mechanisms of DC1 induction will pave the way for a pharmacological modulation of DC, using appropriate small molecules. Further, the present invention allows the identification of a wider panel of type-I IFN-inducing agents able to promote DC1 induction, similar to p-I:C.

DC-based vaccine targets enabled by the present invention include the induction of type-1 immunity against HPV-related antigens in cervical carcinoma patients. Further, the DCs of the present invention provide a tool for understanding of the basic principles of immuno-regulation and the treatment of infections with pathogens resistant to standard forms of treatment, including HIV, CMV, HBV, HCV, or tuberculosis.

Thus, the present invention's disclosure of αDC1s, as powerful in inducers of CTL-, Th1- and NK cell activity, and of CTL-, Th1-, and NK cell-mediated anti-tumor responses, indicate several new therapeutic and preventive possibilities of the current invention in cancer and pre-cancerous states as well as in chronic infectious diseases, atopic allergies, and certain forms of autoimmunity, where type-1 (CTL-, TH1, and NK cell-mediated) immunity can also be beneficial. DC1, especially αDC1 induced in the maturation conditions involving the combination of type I and type II interferons (or their surrogates), can be used as carriers of vaccines, or as the stimulating agents to activate and expand immune cells ex-vivo, for their subsequent use in adoptive immunotherapy. Moreover, the ability of DC1s to act as powerful inducers of T cell responses in vitro, can also be a useful tool for detecting the presence of pathogen-specific T cells in circulation or in human tissues, even when T cells are difficult to detect y standard methods, e.g. due to their suppression, exhaustion or anergization. In addition, high potency of αDC1 in inducing CTL-, Th1- and NK cell activity makes them a useful research tool for the identification of the genes and proteins particularly important in activating the above types of immune cells, facilitating the development of additional, potentially novel targets of immune intervention, and potentially novel factors, that can be used as immunomodulators, either in place of αDC1, as self-standing therapeutic agents, or supplementing other forms of (immuno)therapy.

DESCRIPTION OF PREFERRED EMBODIMENTS

The following is a description of a preferred embodiment of a method for generating DC1s according to the present invention.

Many commercially available media can be used to generate the DCs. By way of example, but not limitation, such media include: IMDM with 10% FBS (both from Gibco, Grand Island, N.Y.), IMDM with 2% HS (Atlanta Biologicals, Atlanta, Ga.; additional, 1% and 10% concentrations of human sera), and serum-free AIM-V medium (Gibco/Invitrogen, Grand Island, N.Y.) or serum-free X-Vivo Medium (Cambrex, East Rutherford, N.J.). Many cytokines, including, but not limited to the following, can be used to obtain immature DCs, induce their final maturation and polarization, and to generate tumor-specific CTLs: rhu GM-CSF and IL-4 (both 1000 IU; Schering-Plough (Kenilworth, N.J.); IFN-α (Intron A-IFN-α-2b; Schering-Plough); IFN-β; (Avonex; Biogen Inc., Cambridge, Mass.); IL-2 (Chiron Corp.; Emeryville, Calif.); rhuTNF-α (Strathmann Biotech Gmbh, Hannover, Germany); rhuIL-1β (Strathmann); rhuIFN-γ (Strathmann); LPS (from *E. coli* 011:B4; Sigma, St. Louis, Mo.); PGE2 (Sigma, St. Louis, Mo.); rhuIL-7 (R&D Systems, Minneapolis, Minn.) poly-I:C (Sigma, St. Louis, Mo.).

According to one embodiment of the present invention, mononuclear cells obtained from the peripheral blood of healthy donors or patients afflicted with a disease of interest, e.g., melanoma, are isolated by density gradient separation using a variety of techniques including Lymphocyte Separation Medium (Cellgro Mediatech, Hemdon, Va.). To obtain immature (Sallusto & Lanzavecchia, 1994), monocytes are isolated from peripheral blood lymphocytes using a Percoll (Sigma) density separation technique, followed by plastic adherence, as described (Kalinski et al., 1997). Monocytes are cultured in well plates (Falcon, Becton Dickinson Labware, Franklin Lakes, N.J.) in individual media supplemented with rhu GM-CSF and IL-4 (both 1000 IU).

CD8$^+$ T cells (96-98% purity) are isolated from PBMCs using a variety of commonly known techniques including the StemSep™ negative selection systems (StemCell Technologies Inc., Vancouver, BC, Canada). Phenotypic analysis is performed using known methodologies including the WinMDI Version 2.8 Software (Joseph Trotter, Scripps Research Institute, La Jolla, Calif.).

A comparison of the induction of DC maturation and polarization according to the present invention and current methods was performed to demonstrate the superiority of the present invention. To conduct such a comparison, DC cultures (performed in either serum-supplemented or serum-free conditions) were exposed to different maturation regimens according to the following protocols: (1) the current "gold standard" of clinically-used DC which provides for DC matured by the "complete cytokine mix": IL-1β, TNFα, IL-6, and PGE$_2$ (control DC; Jonuleit et al., 1997); (2) DC1-inducing protocols previously known in the art which include (a) serum-supplemented cultures: maturation by IL-1β, TNFα, and IFNγ ανδ (b) Serum-supplemented cultures: maturation by LPS and IFNγ; and (3) DC1-inducing protocols of the present invention including (a) serum-free culture (AIM-V medium): maturation by IL-1β, TNFα, IFNγ and IFNα; (b) serum-free culture (AIM-V medium): maturation by IL-1β, TNFα, IFNγ, IFNα and poly-I:C; (c) serum-free culture (AIM-V medium): maturation by IL-1β, TNFα, IFNγ, and poly-I:C; (d) serum-supplemented culture: maturation by IL-1β, TNFα, IFNγ and IFNα; (e) serum-supplemented culture: maturation by IL-1β, TNFα, IFNγ, IFNα and poly-I:C; and (f) serum-supplemented culture: maturation by IL-1β, TNFα, IFNγ, and poly-I:C.

A range of concentrations of each of the above factors can be used (from 0.1 pg/mL to 10 mg/mL. One preferred embodiment, depicted herein, uses the following concentrations of the above factors: IL-1β (25 ng/ml); TNFα (50 ng/ml), IFNγ (1000 U/ml); poly-I:C (20 μg/ml); IFNα (3000 U/ml); LPS (250 ng/ml). In an assay employing this preferred embodiment, the DC cells produced by the disclosed protocols were harvested and analyzed for the expression of maturation-associated surface markers, the ability to produce IL-12p70, and to induce melanoma-specific CTLs. To test and demonstrate the IL12p70-producing capacity of DC, they were harvested, washed, and plated in flat bottom well plates. To mimic the interaction with CD40L expressing Th cells, CD40L-transfected J558 cells (University of Birmingham, Birmingham, UK) were added (Cella et al., 1996). Supernatants were collected and tested for the presence of IL-12p70 by ELISA.

Negatively-isolated CD8.sup.+ T cells from HLA-A2.sup.+ donors were sensitized by the individual populations (non-polarized and polarized) of autologous DC pulsed with the HLA-A2-restricted peptides MART-1 (27-35, AAGIGILTV, SEQ ID NO: 1), gp100 (209-217, ITDQVPFSV, SEQ ID NO: 2, and 154-162, KTWGQYWQV, SEQ ID NO: 3), and tyrosinase (368-376, YMNGTMSQV, SEQ ID NO:4). RhuIL-2 (50 U/ml) was added and the differentially-sensitized CD8.sup.+ T cell cultures were expanded by an additional round of stimulation, using peptide-pulsed autologous PBMC. The differentially-induced CD8.sup.+ T cell lines were stimulated with peptide-pulsed HLA-A2$^+$ T2 cells to monitor the frequency of the melanoma-specific CD8.sup.+ T cells by IFN-γ. ELISPOT. Cytolytic activity of the differentially-sensitized CTL cultures was determined by performing standard .sup.51Cr-release assays with results calculated and reported in the percent of target lysis at individual effector-to-target ratios as described (Friberg et al., 1996). Concentrations of IL-12p70 in cell supernatants were determined by specific ELISAs, performed with matched antibody pairs, standards, and reagents.

The presence of IFNγ during DC maturation induced by IL-1β and TNFα, or induced by LPS, results in the development of stable type-1-polarized DC (DC1), characterized by high ability to produce IL-12p70 upon subsequent stimulation (FIG. 1), and by mature phenotype (FIG. 2). Although the expression of surface maturation-associated markers on DC1 is similar to IL-1β/TNFα/IL-6/PGE$_2$-matured control DCs (cDCs), their IL-12-producing capacity is at least 1-log higher. Both DC1s and cDCs uniformly expressed CCR7, the predictive marker of their ability to migrate to the lymph nodes, indicating their utility in vaccines.

Although it has been previously demonstrated that DC1s show superior ability to induce Th1 cytokine profiles in naïve CD4$^+$ T cells (Vieira et al., 2000, Mailliard et al., 2002), the present invention discloses a method that uses DC1s as superior inducers of CTL-responses against melanoma-related antigens in healthy donors and melanoma patients. A single round of short-term stimulation of CD8$^+$ T cells, results in the induction of strongly elevated numbers of IFNγ-producing MART-1-specific, CTLs in the blood of healthy donors (FIG. 3). The most pronounced differences were observed in the case of long-lived CTL responses, when the differential sensitization with DC1s as opposed to cDC was followed by the subsequent expansion of the differentially-induced CTL lines (on autologous PBMCs), to mimic the situation when vaccine-induced CTLs will need to be sustained by endogenous APCs in cancer-affected patients (FIG. 3). A preferred embodiment of the present invention using the blood of two melanoma patients, provides for DC1 that induce superior expansion of melanoma-specific CTLs, against MART-1, tyrosinase and gp100 (FIG. 4). After a single round of differential IVS, a 4- to 8-fold higher frequency of DC1-induced peptide-specific CTL is observed, the advantage of using DC1 is more evident after secondary restimulation of the differentially-sensitized cultures with peptide-pulsed autologous PBMC, reflecting the enhanced persistence of the DC1-induced CTL responses according to the present invention. The overall magnitude of such responses is over 50-fold higher than in control cultures (FIG. 4). Induction of long-lived CTL responses against multiple MAAs indicates that DC1s of the present invention are highly suitable to induce meaningful anti-tumor responses in vivo, which will have beneficial therapeutic effects in patients with cancer.

According to the methods of the present invention, IFNα and p-I:C synergize with an IFNγ-based polarizing cocktail to generate DC1 in serum-free conditions. The combination of IFNγ with IL-1β and TNFα allows the development of mature DC1 in the fetal calf serum (FCS)-supplemented media, but not in the presence of human serum, nor in serum-free AIM-V medium (FIG. 5). In contrast, the addition of IFNγ to the widely used "complete cytokine mix" (IL-1β/TNFα/IL-6/PGE$_2$; Jonuleit et al., 1997) is ineffective in the induction of high IL-12 producing DC1 in serum-free conditions (FIG. 5).

Although neither IFNα nor poly-IC alone (nor in combination with IL-1β and TNFα) promote the induction of DC1 (Vieira et al., 2000, current data not shown), pursuant to methods of the present invention, the addition of each IFNα and to a lesser extent poly I:C to the cocktail of IFNγ, IL-1γ, and TNFα, provides for a serum-independent development of DC1 with a strongly enhanced ability to produce IL-12p70 after subsequent stimulation (FIG. 6). In a most preferred embodiment, both IFNα and poly-IC are present. Further, the presence of IFNα and poly-I:C during DC maturation individually or in combination, enhance the already high IL-12-producing capacity of the DC1 obtained in the presence of FCS.

Serum-free DC1s obtained in the presence of all five factors (IFNγ, IL-1β, TNFα, IFNα, and poly-I:C) show a similar fully-mature surface phenotype as control DC (matured by the "complete cytokine mix": IL-1β, TNFα, IL-6, and $PGE_2$), or DC1 induced by LPS and IFNγ in FCS-supplemented medium, showing similar expression levels of such maturation-associated markers as CD83, CD86 and CCR7 (FIG. 7). The fully-mature DC phenotype exist when both IFNα and poly-IC are present (FIG. 7).

Alpha type-1 DC (αDC1) of the present invention have a superior ability to induce melanoma-specific CTL responses. To analyze their CTL-inducing activity, individual populations of DC1 (generated under serum-free, or serum-supplemented conditions), or serum-free control IL-1β/TNFα/IL-6/$PGE_2$-matured cDC, were pulsed with melanoma-associated antigenic peptides, and used to sensitize autologous $CD8^+$ T cells from HLA-$A2^+$ melanoma patients. The long-term $CD8^+$ T cell lines obtained by further expansion with autologous PBMCs were harvested and used as responder cells against T2 cells pulsed with individual peptides, or their combination. As shown in FIG. 8, each of the DC1s obtained in each of the protocols tested induced significantly higher numbers of melanoma specific (MART-1-, gp100-, and tyrosinase-specific) $CD8^+$ T cells, when compared to the DCs matured in the presence of IL-1β/TNFα/IL-6 and $PGE_2$ ("control DC": Jonuleit et al, 1997). In addition, to being superior to control DCs in the induction high numbers of melanoma-specific $CD8^+$ T cells, alpha-type-1 DC also proved superior in the induction of high cytotoxic activity against target cells pulsed with MAA peptides (FIG. 9).

In addition to being superior inducers of the cytolytic activity of tumor-specific CD8+ T cells (CTLs), αDC1 also proved superior in their ability to induce similar, cytolytic functions in $CD4^+$ Th cells, and in isolated NK cells, allowing them to efficiently kill transformed cells (FIG. 10).

Of particular importance for their ability to function in vivo, as carriers of anticancer vaccines, αDC1 can effectively migrate in response to CCR7 ligands (FIG. 11A), known to be produced in the T cell areas of the lymph nodes and to be responsible for the local accumulation of immune cells. Importantly, exclusively αDC1, but not standard mature DCs nor immature DCs could produce IL-12p70 in response to CD40L stimulation, following their CCR7-ligand-induced migration (FIG. 11B).

The current description of αDC1, as powerful in inducers of CTL-, Th1- and NK cell activity, and of CTL-, Th1-, and NK cell-mediated antitumor responses, indicate several new therapeutic and preventive possibilities of the current invention in cancer and precancerous states as well as in chronic infectious diseases, atopic allergies, and certain forms of autoimmunity, where type-1 (CTL-, Th1, and NK cell-mediated) immunity can be beneficial. DC1, especially αDC1 induced in the maturation conditions involving the combination of type I and type II interferons (or their surrogates), can be used as carriers of vaccines, or as the stimulating agents to activate and expand immune cells ex-vivo, for their subsequent use in adoptive immunotherapy. Moreover, the ability of DC1 to act as powerful inducers of T cell responses in vitro, can also be a useful tool for the detecting the presence of pathogen-specific T cells in circulation or in human tissues, even in cases when T cells are difficult to detect y standard methods, e.g. due to their suppression, exhaustion or anergization. In addition, high potency of αDC1 in inducing CTL-, Th1- and NK cell activity makes them a useful research tool for the identification of the genes and proteins particularly important in activating the above types of immune cells, facilitating the development of additional, potentially novel targets of immune intervention, and potentially novel factors, that can be used as immunomodulators, either in place of αDC1, as a self-standing therapeutic agents, or supplementing other forms of (immuno)therapy.

SEQUENCE LISTING

<160> NUMBER OF SEQ ID NOS: 4

Figure 1:
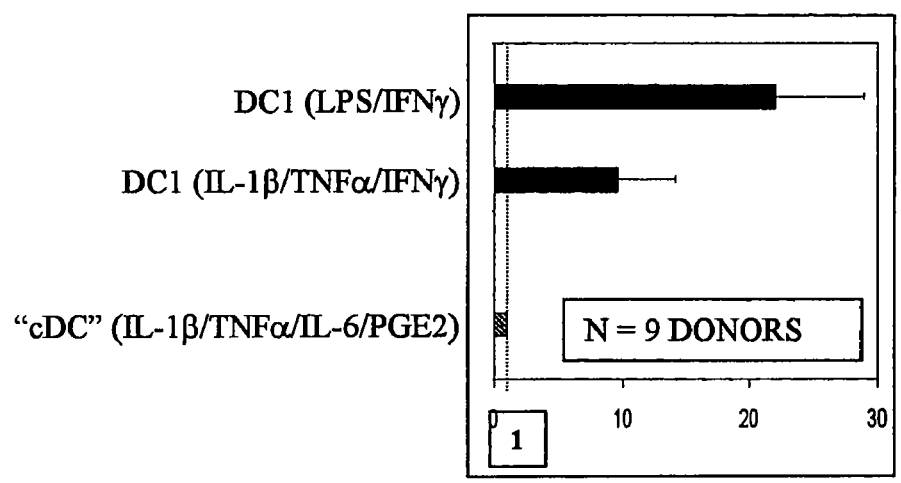
FIG. 1. DC1 of the present invention show strongly upregulated ability to produce IL-12p70. DC1 or cDC induced in 48 hour-long maturation cultures, were washed, counted and stimulated with CD40L-transfected J558 cells. 24 hour supernatants were analyzed for IL-12p70 contents with IL-12p70 ELISA. DC1 were obtained in FCS-supplemented medium and matured under the influence of IL-1β/TNFα and IFNγ Control DC, obtained in serum-free medium (AIM-V) were matured by IL-1β/TNFα/IL-6/$PGE_2$. (See Materials and Methods for the concentrations of the individual DC1-maturation-inducing factors, PGE2 was used at $10^{-6}$M, IL-6 was used at 1000 units/mL). The data obtained from 9 different donors is shown as the ratios of the levels of IL-12p70 produced by DC1 of the present invention compared to the levels of IL-12p70 production by control DC.
Figure 2:
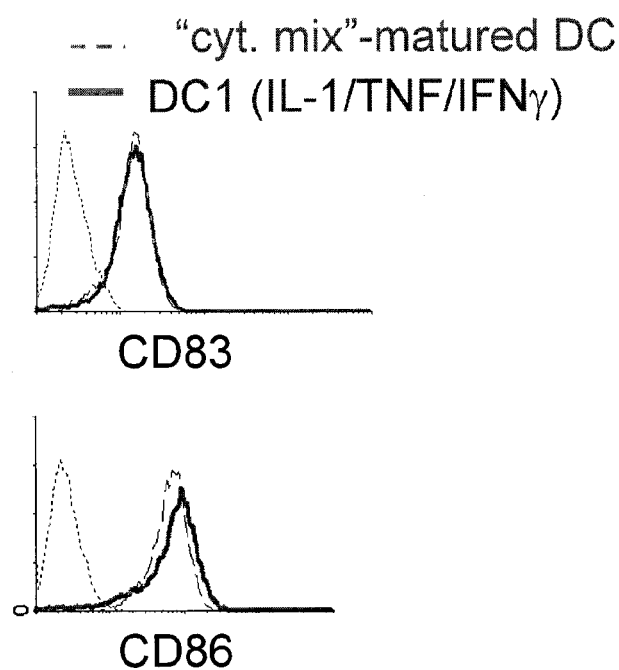
FIG. 2. (A). DC1 of the present invention and control DC express similar levels of the maturation-associated markers: CD83 and CD86. (B). DC1 uniformly express CCR7. 48 hour-long maturation cultures: DC1 were obtained in FCS-supplemented medium and matured under the influence of IL-1β/TNFα and IFNγ. cDC were grown in serum-free conditions and matured by IL-1β/TNFα/IL-6/PGE2.
Figure 2:
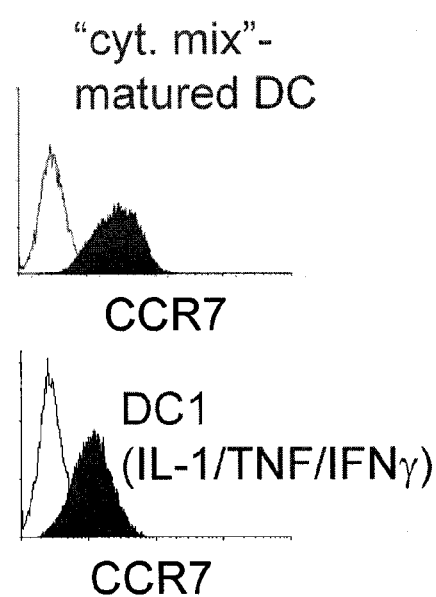
Figure 3:
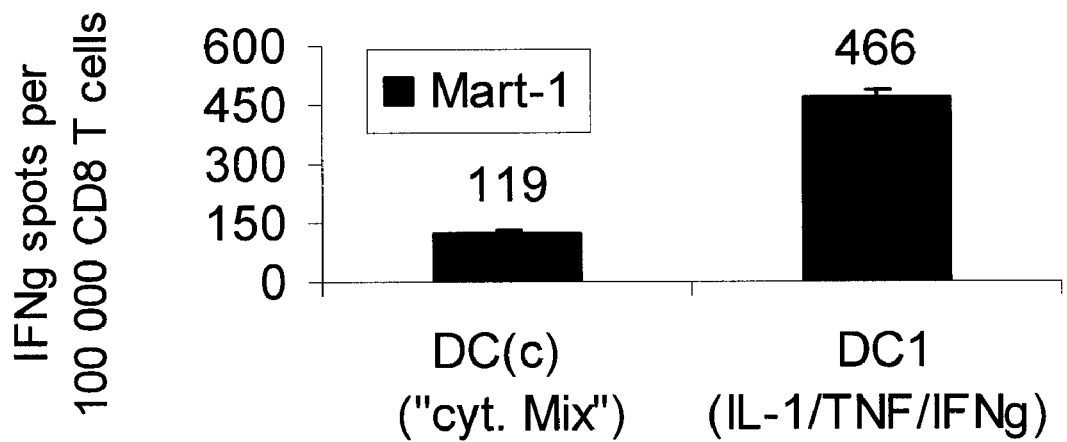
FIG. 3. Polarized DC1 induce stronger responses of MART-1-specific $CD8^+$ CTLs. $CD8^+$ T cells from a HLA-$A2^+$ healthy donor were primed with MART-MHC class I-restricted peptide presented either by DC1 (obtained the standard protocols in the presence of serum) or standard cDC. At day 14 and day 28, the expanded CTL cultures were tested for specific responses against MART-1. Left: 1 round of IVS, using DC1 or cDC matured by IL-1/TNF/IL-6/PGE2. Right: 1 round of IVS with DC1 as compared to cDC, followed by second round of stimulation with peptide-pulsed PBMC, to demonstrate the persistence of the DC-induced specific CTLs. In both cases, the ELISPOT assay was performed using the peptide-pulsed T2 cells. Non-peptide-coated T2 cells served as nonspecific control. The levels of nonspecific responses (to peptide-unpulsed T2 cells) were subtracted. Similar data was obtained using the blood from two additional healthy donors.
Figure 3:
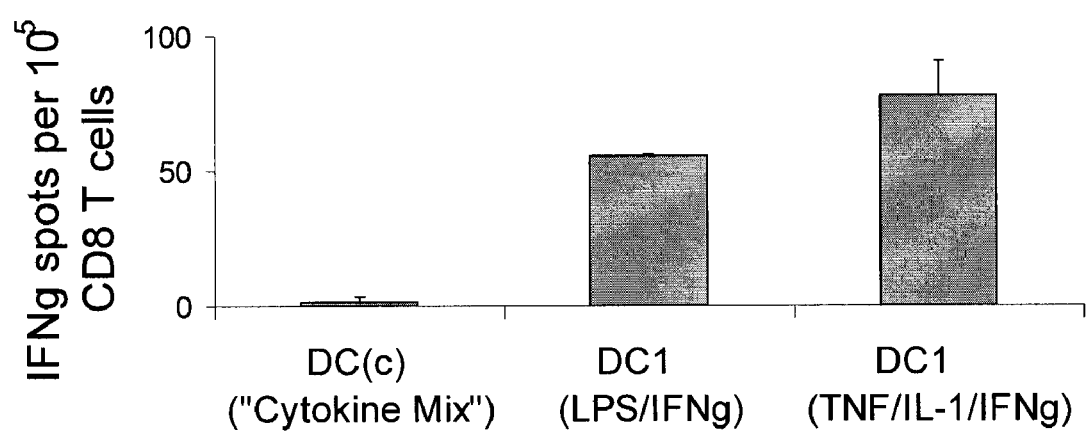
Figure 4:
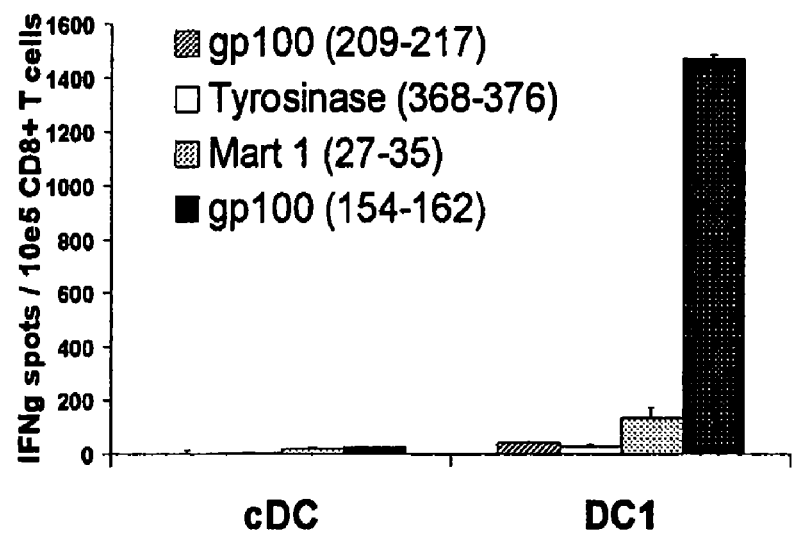
FIG. 4. DC1 generated from melanoma patients show superior ability to induce $CD8^+$ T cell responses against multiple melanoma-specific epitopes. DC1 (induced by LPS/IFNγ) or IL-1β/TNFα/IL-6/$PGE_2$-matured cDC, generated from an HLA-$A2^+$ melanoma patient, were pulsed with a mix of the 4 melanoma-associated antigenic peptides, washed, counted and co-cultured with negatively-isolated $CD8^+$ T cells and (irradiated) CD40L-tansfected J558 cells as a surrogate source of CD40L-mediated helper signals. The differentially-sensitized $CD8^+$ T cells, were further expanded by restimulation (d14) with irradiated autologous PBMCs pulsed with the same mix of peptides. At day 28, CTL lines were harvested, washed, and used as responder cells against T2 cells pulsed with individual peptides (nonspecific T2 cells served as nonspecific control, which was subtracted).
Figure 5:
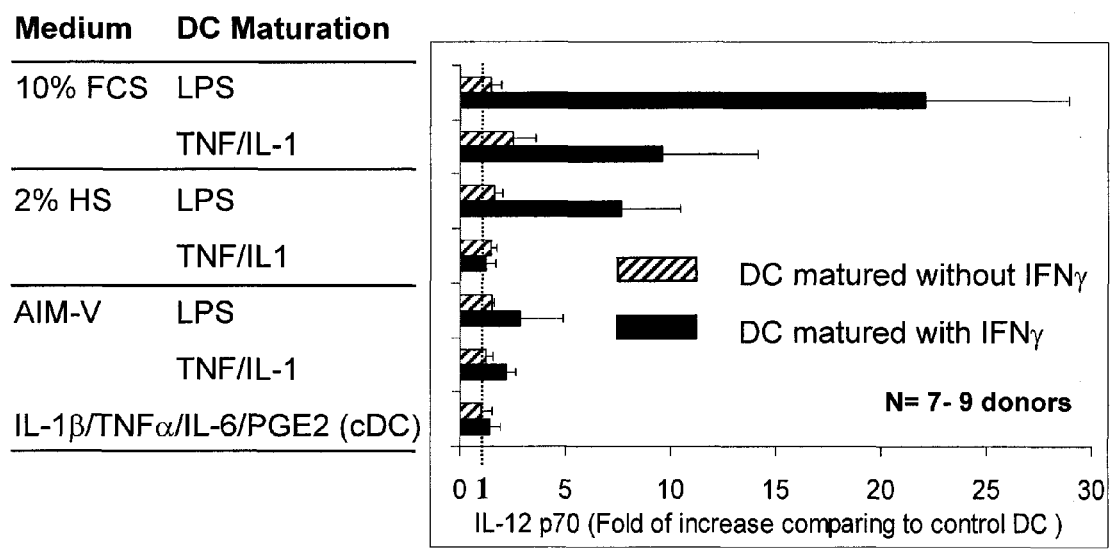
FIG. 5. "Traditional" type-1-polarizing protocols do not support the induction of DC1 in serum-free medium. DCs grown in media supplemented with FCS (10%), HS (2%)-, or in serum free medium (AIM-V) were matured in different "traditional protocols" either in the absence or in the presence of the DC1-polarizing factor; IFNγ. Following 48 hour-long maturation, DC were washed, counted and stimulated with CD40L-transfected J558 cells. 24 hour supernatants were analyzed for IL-12p70 contents with IL-12p70 ELISA. The data are shown as a summary of data obtained from 7-9 different donors. In each experiment, the levels of IL-12p70 produced by DC1 were compared to the levels of IL-12 production by control DC (DC matured in IL-1β/TNFα/IL-6/PGE$_2$). In case of the human serum, its additional concentrations (1% and 10%; using several different batches of serum from different suppliers, yielded similar negative results (data not shown).
Figure 6:
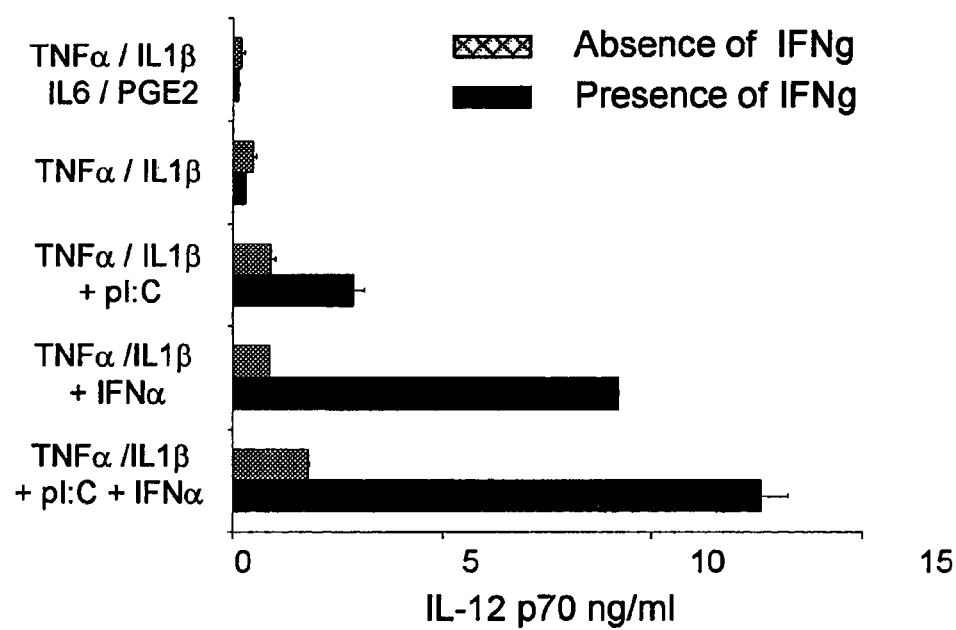
FIG. 6. Novel Serum Free Protocols of DC1 generation. The addition of IFNα (and to a lesser extent of poly I:C) to DC maturation-inducing cytokines (IL-1β/TNFα/IFNγ) allows the induction of DC1 in serum free culture conditions. In all cases, 24 h-matured DCs were harvested, washed and stimulated with CD40L to induce IL-12 production. Please, note that the optimal expression of all of the maturation-associated maturation markers required the participation of all 5 components of the "alpha-type-1"-polarizing cocktail. The data are from a representative experiment of five.
Figure 7:
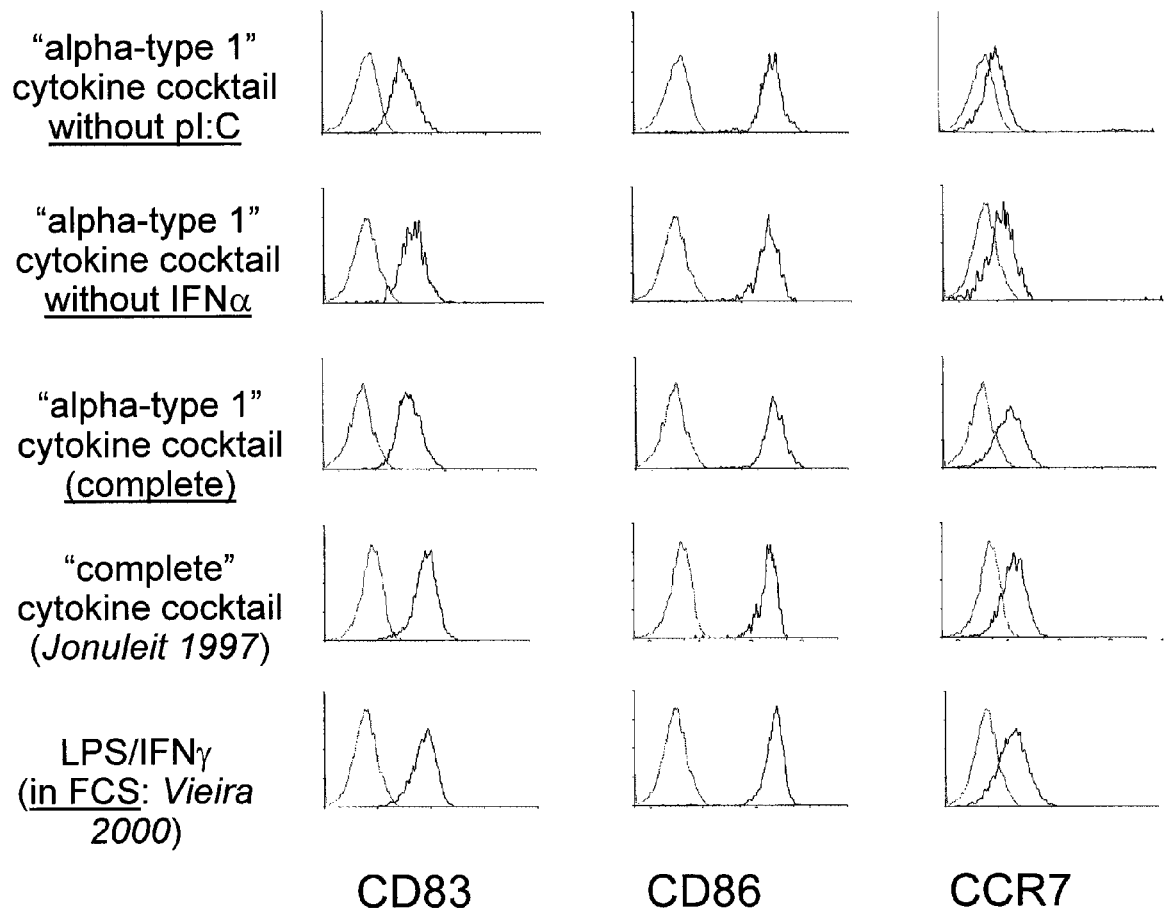
FIG. 7. Fully-mature status of "alpha type-1" DC (αDC1) obtained in serum-free media. Expression of the maturation-associated markers (CD83, CD86, and CCR7) on cDC (IL-1β/TNFα/IL-6/PGE$_2$-matured DC), DC1 induced in serum-supported protocol, and serum-free DC1 (induced by IL-1β/TNFα/p-I:C/IFNα, and IFNγ,) data from a representative of three experiments, that all gave similar results. Please, note that the optimal expression of all of the maturation-associated maturation markers required the participation of all 5 components of the "alpha-type-1"-polarizing cocktail. Similar data were obtained in at least three additional experiments.
Figure 8:
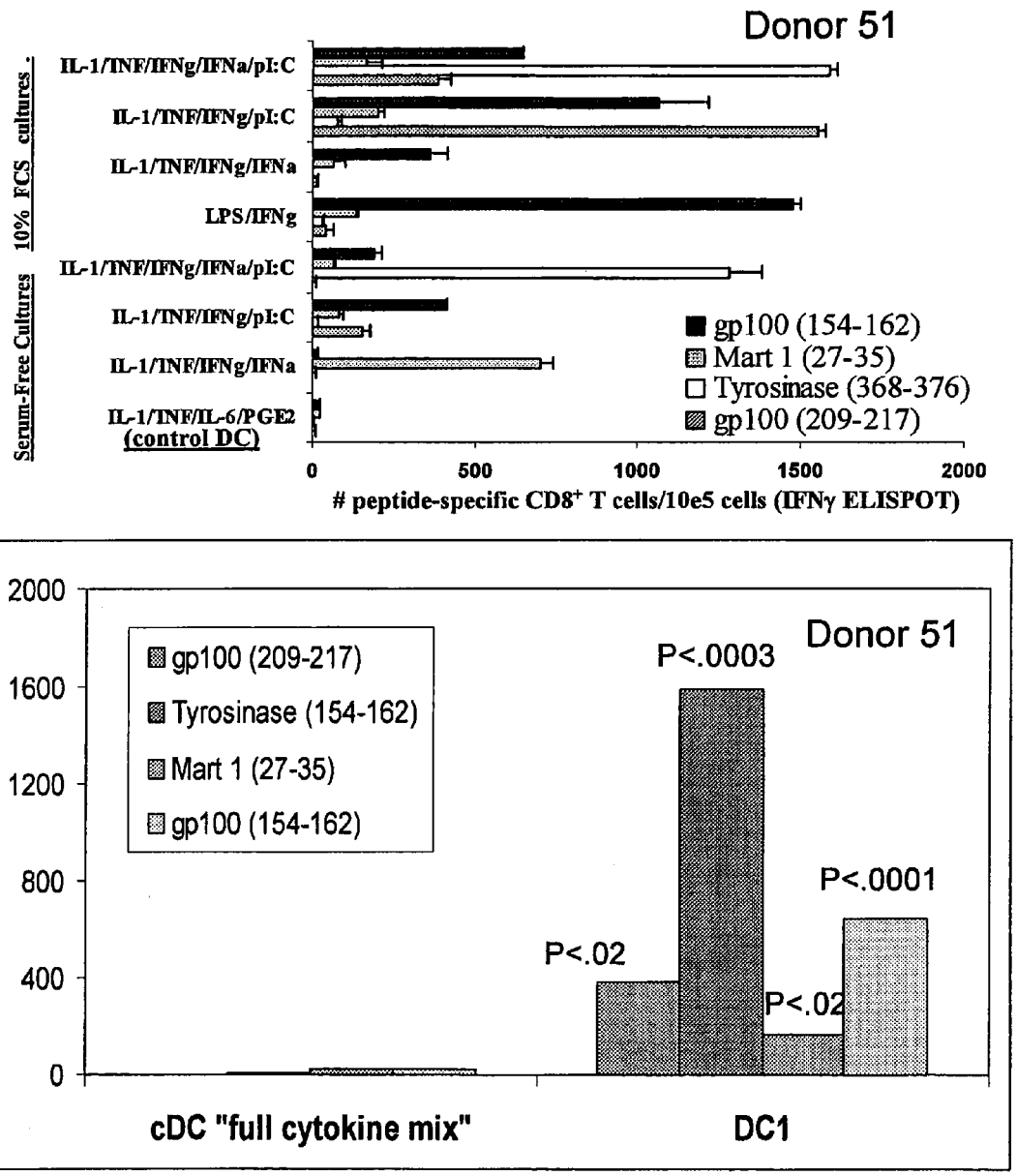
FIG. 8. Alpha type-1 DC (αDC1), generated from melanoma patients in serum-free conditions (an in serum-supplemented media) show superior ability to induce CD8$^+$ T cell responses against multiple melanoma-specific epitopes, when compared to the currently-applied DCs. Individual populations of DC1 (generated under serum-free, or serum-supplemented conditions), or serum-free control IL-1β/TNFα/IL-6/PGE$_2$-matured cDC, were pulsed with melanoma-associated antigenic peptides, and used to sensitize autologous CD8$^+$ T cells from HLA-A2 melanoma patient. In brief, DCs were pulsed with a mix of the 4 melanoma-associated antigenic peptides [MART-1 (27-35), gp100 (209-217 & 154-162), tyrosinase (368-376)], washed, counted and co-cultured with negatively-isolated CD8$^+$ T cells and (irradiated) CD40L-tansfected J558 cells as a surrogate source of CD40L-mediated helper signals. The resulting differentially-sensitized CD8$^+$ T cell lines were further expanded by restimulation (d14) with irradiated autologous PBMCs pulsed with the same mix of peptides, and at day 28, they were harvested, washed, and used as responder cells against T2 cells pulsed with individual peptides The levels of nonspecific background (obtained with peptide-unpulsed T2 cells) were subtracted. (nonpulsed T2 cells served as nonspecific control, which was subtracted). A. Analysis of the responses to individual MAA peptides; top: Comparison of the CTL-inducing cultures utilizing individual serum-free and serum-supplemented protocols of DC generation; bottom: back-to-back comparison of CTL-inducing efficacy of cDC and alpha type-1 DC (αDC1) generated in serum-free conditions. B. αDC1 are highly-efficient cross-presenting cells. Apoptotic melanoma cells (FEM-X) were fed to immature DCs or αDC1 generated from the blood of healthy HLA-A2+ donor and used to prime autologous CD8+ T cells (see directly above). At day 28, the numbers of IFNγ-producing CD8+ T cells recognizing the original melanoma cell line (FEM-X), or T2 cells pulsed with a defined melanoma associated epitope (MART 27-35). The levels of nonspecific IFNγ-producing cells (obtained respectively with non-HLA-A2-expressing melanoma cell line, or with T2 cells pulsed with melanoma-nonrelevant peptide) were subtracted.
Figure 8:
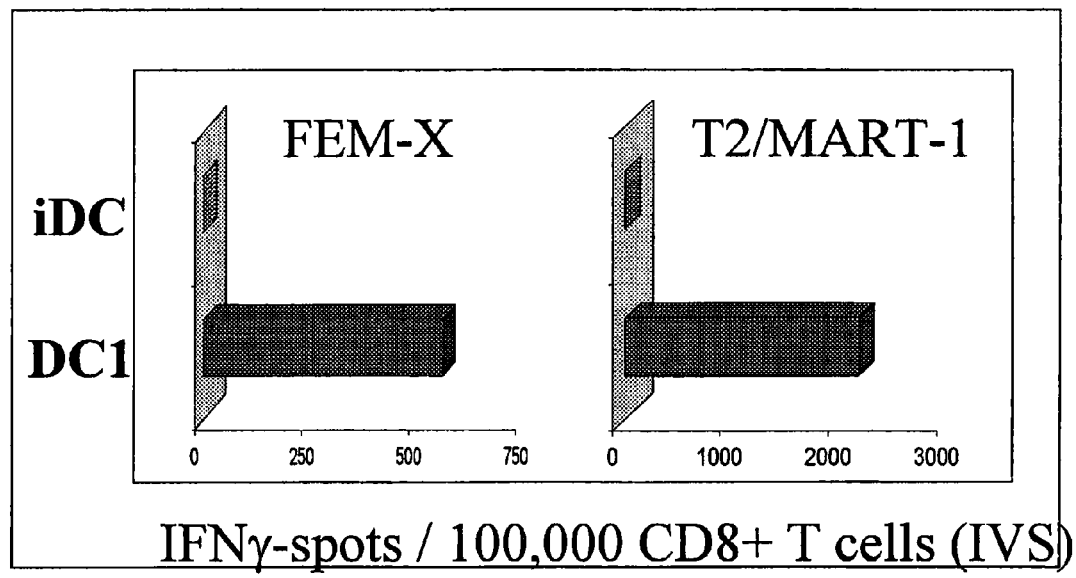
Figure 9:
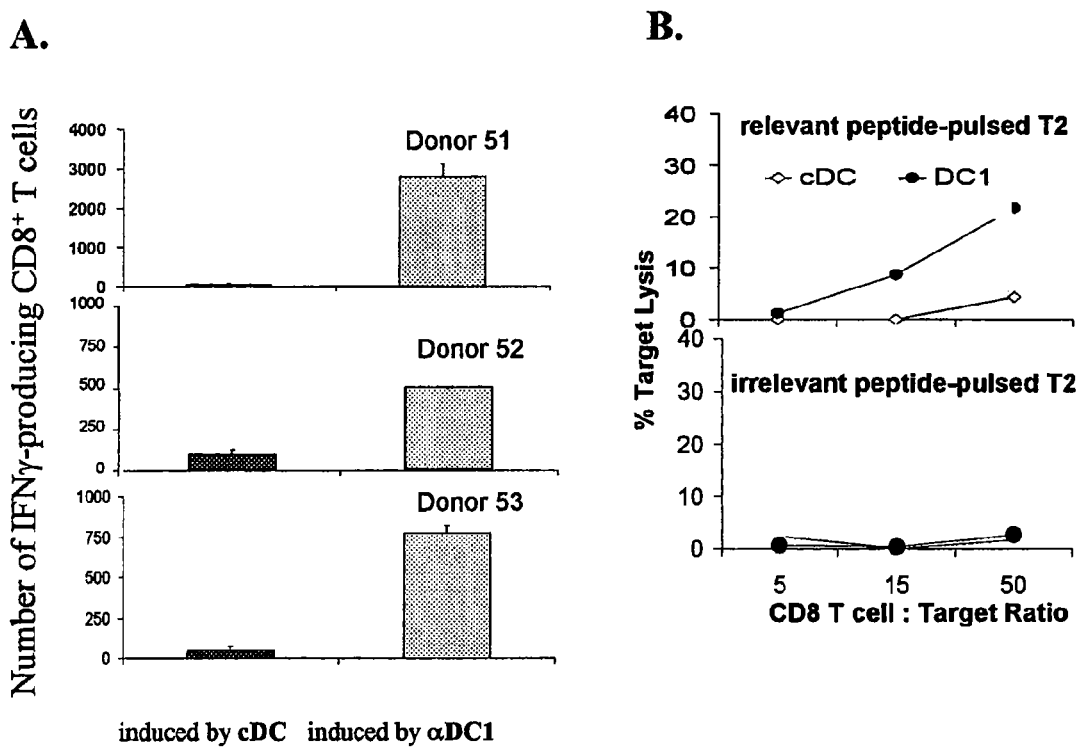
FIG. 9. Alpha type-1 DC (αDC1) show superior ability to induce cytotoxic T cell (CTL) responses against multiple melanoma-specific epitopes, when compared to the currently-applied DCs. Alpha type-1 DC (αDC1), generated under serum-free conditions, or IL-1/TNF/IL-6/PGE$_2$-matured cDC, were pulsed with melanoma-associated antigenic peptides [MART-1 (27-35), gp100 (209-217 & 154-162), tyrosinase (368-376)], and used to sensitize autologous CD8$^+$ T cells from HLA-A2$^+$ melanoma patient (see the legend to FIG. 8 for the experimental details). A. The cumulative responses of differentially sensitized T cells (at day 28 post IVS) to all of the peptides used for in vitro sensitization, in 3 patients with stage II-stage IV melanoma (IFNγ ELISPOT). The levels of nonspecific backgrounds were subtracted. B. To analyze their cytotoxic (CTL) activity, the differentially-induced CD8$^+$ T cells were harvested at day 28, washed, and used as effector cells against $^{51}$Cr-labelled T2 cells pulsed with all MAA antigenic peptides as target cells (Top). Bottom: The levels of nonspecific killing (obtained with irrelevant peptide-unpulsed T2 cells) were low and similar in all cases.
Figure 10:
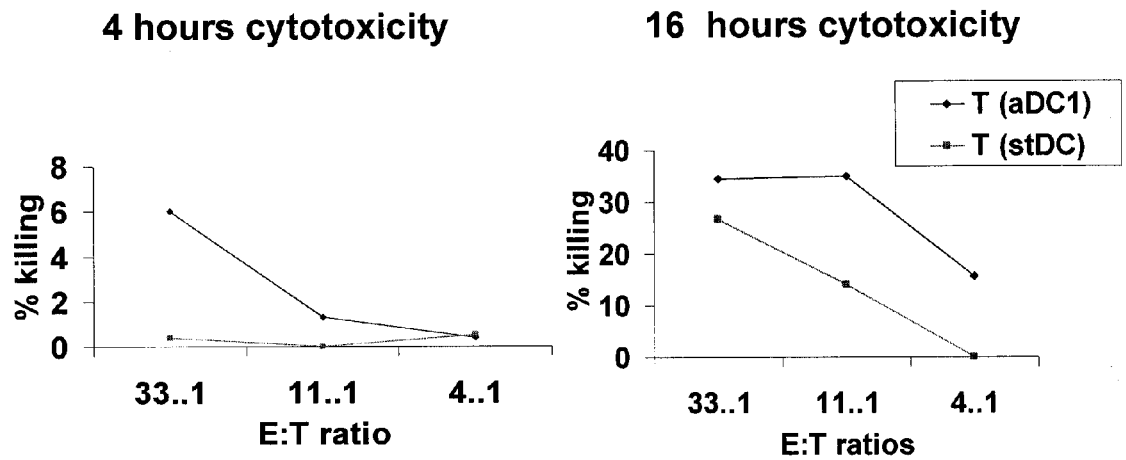
FIG. 10. Mature αDC1 generated in serum-free cultures are superior inducers of cytotoxic activity of CD4+ T cells and NK cells against tumor cells. A. Standard DC (IL-1β/TNFα/IL-6/PGE$_2$-matured DC) and αDC1 induced in serum free cultures by IL-1β, TNFα, p-I:C, IFNα, and IFNγ, were loaded with superantigen (SEB) and used to prime freshly-isolated CD4+ T cells. After two week expansion of CD4+ T cell cultures, the cytotoxic potential of differentially-primed CD4+ T cells was tested in 4 hour or 16 hour chromium release assay, using SEB-coated melanoma cells as targets. Data from a representative experiment of 3. B. NK cell activating potential of differentially-matured DCs. C. Cytotoxic activity of NK cells against chromium-labeled K562 target cells, either without prestimulation or prestimulated overnight by (left) serum free generated αDC1 (IL-1β/TNFα/IFNα/p-I:C/IFNγ-induced DC1) and standard DCs (IL-1β/TNFα/IL-6/PGE$_2$-matured DC) or (right) traditional DC1 (generated in FCS-supplemented cultures and matured with LPS and IFNγ) or standard (IL-1β/TNFα/IL-6/PGE$_2$-matured) DC generated in the presence of FCS. 4 hour-long chromium release assay at 10:1 T:T ratio. Data from one of two experiments that both showed similar results.
Figure 10:
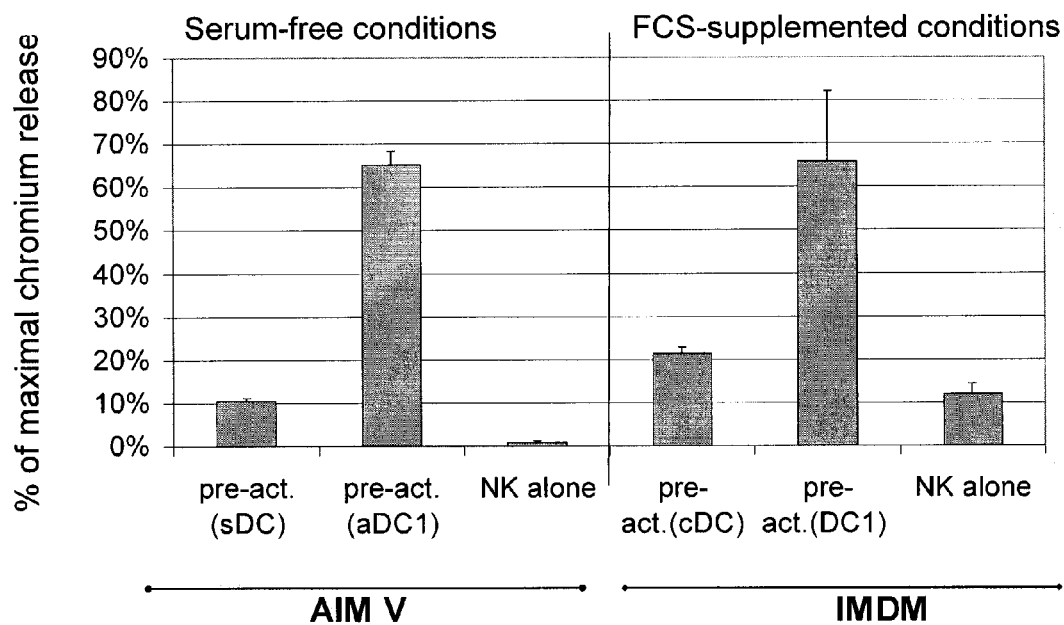
Figure 11:
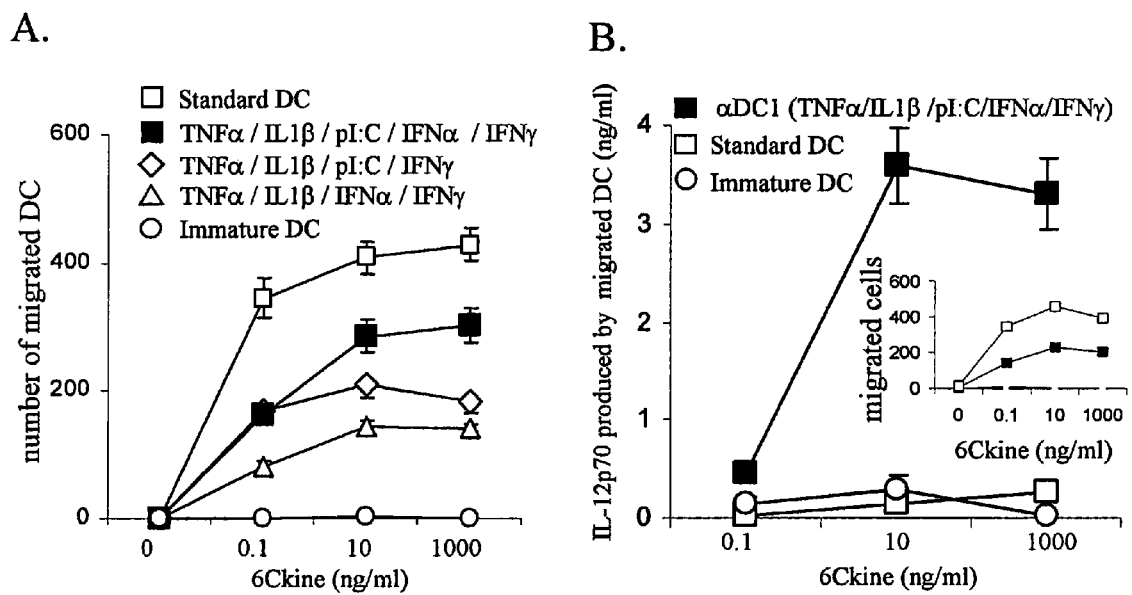
FIG. 11. Mature αDC1 generated from melanoma patients in serum-free cultures are highly-responsive to 6C-kine and maintain high IL-12p70 producing capacity following migration. A. 6C-kine-induced migration of differentially-matured DCs. B. IL-1β/TNFα/IFNα/p-I:C/IFNγ-induced αDC1 (but not standard DCs nor iDC) retain their ability to produce high levels of IL-12p70 in response to CD40-ligatior, following the migration in 6C-kine gradients. The inset: The corresponding relative numbers of DCs migrating in response to 6C-kine.

<210> SEQ ID NO 1
<211> LENGTH: 9
<212> TYPE: PRT
<213> ORGANISM: Homo sapiens

<400> SEQUENCE: 1

Ala Ala Gly Ile Gly Ile Leu Thr Val
1               5

<210> SEQ ID NO 2
<211> LENGTH: 9
<212> TYPE: PRT
<213> ORGANISM: Homo sapiens

<400> SEQUENCE: 2

Ile Thr Asp Gln Val Pro Phe Ser Val
1               5

<210> SEQ ID NO 3
<211> LENGTH: 9
<212> TYPE: PRT
<213> ORGANISM: Homo sapiens

<400> SEQUENCE: 3

Lys Thr Trp Gly Gln Tyr Trp Gln Val
1               5

<210> SEQ ID NO 4
<211> LENGTH: 9
<212> TYPE: PRT
<213> ORGANISM: Homo sapiens

<400> SEQUENCE: 4

Tyr Met Asn Gly Thr Met Ser Gln Val
1               5

What is claimed is:

1. A method for the production of dendritic cells, comprising adding in vitro a) an effective amount of interferon (IFN)-α or IFN-β and b) an effective amount of IFN-γ to a population of immature dendritic cells from a subject of interest; and culturing the immature dendritic cells in vitro to produce mature dendritic cells, wherein after subsequent stimulation of the mature dendritic cells with CD40 ligand, said mature dendritic cells produce more IL-12p70 as compared to immature dendritic cells stimulated with CD40 ligand.

2. The method of claim 1, wherein the method comprises adding a) 0.1 pg/ml to 10 mg/ml of IFN-α or IFN-β and b) 0.1 pg/ml to 10 mg/ml of IFN-γ to the population of immature dendritic cells.

3. The method of claim 1, wherein the method comprises adding a) 0.1 pg/ml to 10 mg/ml of IFN-α and b) 0.1 pg/ml to 10 mg/ml of IFN-γ to the population of immature dendritic cells.

4. The method of claim 1, wherein the method further comprises adding an effective amount of lipopolysaccharide (LPS) to the immature dendritic cells in vitro.

5. The method of claim 1, wherein the method further comprises adding an effective amount of interleukin-1β, tumor necrosis factor (TNF)-α or both to the immature dendritic cells in vitro.

6. The method of claim 1, wherein the immature dendritic cells are cultured in a serum-free medium.

7. The method of claim 1, wherein the dendritic cells produce IL-12p70 at least 10-fold higher than dendritic cells from the subject of interest matured in the presence of IL-1β, TNF-α, IL-6 and prostaglandin (PG) $E_2$.

8. The method of claim 1, wherein the method comprises adding 25 ng/ml IL-1β, 50 ng/ml TNF-α, 1000 U/ml IFN-γ, 20 μg/ml poly-I:C, and 3000 U/ml IFN-α to the immature dendritic cells.

9. The method of claim 1, comprising adding an effective amount of a) IFN-α or IFN-β b) an effective amount of IFN-γ, and c) an effective amount of poly-I:C to the immature dendritic cells in vitro.

10. The method of claim 1, wherein the mature dendritic cells that produce IL-12 migrate in response to a CCR7 ligand.

11. The method of claim 1, wherein the mature dendritic cells that produce IL-12 also express CD83, CD86 and CCR7 on their cell surface.

12. The method of claim 1, further comprising adding c) an effective amount of tumor necrosis factor (TNF)-α, lipopolysaccharide (LPS), Poly I:C, or a combination thereof to the population of immature dendritic cells in vitro.

13. A method for the production of mature dendritic cells, comprising
    isolating immature dendritic cells from a sample of peripheral blood obtained from a subject;
    contacting the immature dendritic cells with a) an effective amount of exogenous interferon (IFN)-α or IFN-β and b) an effective amount of exogenous IFN-γ; and
    contacting the immature dendritic cells with an antigen of interest that binds the Major Histocompatibility Complex (MHC),
    thereby producing mature dendritic cells that present the antigen of interest, wherein after subsequent stimulation of the mature dendritic cells with CD40 ligand, said mature dendritic cells produce more IL-12p 70 as compared to immature dendritic cells stimulated with CD40 ligand.

14. The method of claim 13, wherein the antigen is tumor-specific or specific for an infectious agent.

15. The method of claim 13, wherein the method comprises contacting immature dendritic cells with a) 0.1 pg/ml to 10 mg/ml of IFN-α or IFN-β and b) 0.1 pg/ml to 10 mg/ml of IFN-γ.

16. The method of claim 13, wherein the method comprises contacting the immature dendritic cells with a) 0.1 pg/ml to 10 mg/ml of IFN-α and b) 0.1 pg/ml to 10 mg/ml of IFN-γ.

17. The method of claim 13, wherein the method comprises contacting the immature dendritic cells with 25 ng/ml IL-1β, 50 ng/ml TNF-α, 1000 U/ml IFN-γ, 20 μg/ml poly-I:C, and 3000 U/ml IFN-α.

18. A method for producing activated cytotoxic T cells, comprising,
    producing mature dendritic cells; and
    contacting the mature dendritic cells with CD8+ T cells, thereby producing activated cytotoxic T cells.

19. The method of claim 18, wherein the mature dendritic cells and the CD8+ T cells are induced in vitro.

20. The method of claim 18, comprising contacting the immature dendritic cells with 25 ng/ml IL-1β, 50 ng/ml TNF-α, 1000 U/ml IFN-γ, 20 μg/ml poly-I:C, and 3000 U/ml IFN-α.

* * * * *